United States Patent
Stettler et al.

(10) Patent No.: US 10,159,640 B2
(45) Date of Patent: Dec. 25, 2018

(54) PREBIOTIC ORAL CARE COMPOSITIONS CONTAINING AMINO ACIDS

(71) Applicants: COLGATE-PALMOLIVE COMPANY, New York, NY (US); KATHOLIEKE UNIVERSITEIT LEUVEN, Leuven (BE); UNIVERSITEIT GENT, Gent (BE)

(72) Inventors: Hans Stettler, Hoboken, NJ (US); Wim Teughels, Everberg (BE); Marc Quirynen, Heverlee (BE); Nico Boon, Oosterzele (BE)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/108,105

(22) PCT Filed: Dec. 27, 2013

(86) PCT No.: PCT/US2013/077920
§ 371 (c)(1),
(2) Date: Jun. 24, 2016

(87) PCT Pub. No.: WO2015/099753
PCT Pub. Date: Jul. 2, 2015

(65) Prior Publication Data
US 2016/0324766 A1 Nov. 10, 2016

(51) Int. Cl.
| | | |
|---|---|---|
| A61K 38/05 | (2006.01) |
| A61K 8/99 | (2017.01) |
| A61K 8/64 | (2006.01) |
| A61Q 11/00 | (2006.01) |
| A61K 35/74 | (2015.01) |
| A61K 35/744 | (2015.01) |
| A61K 9/00 | (2006.01) |
| A61K 35/741 | (2015.01) |
| A61K 35/00 | (2006.01) |

(52) U.S. Cl.
CPC .......... *A61K 8/99* (2013.01); *A61K 8/64* (2013.01); *A61K 9/0063* (2013.01); *A61K 35/74* (2013.01); *A61K 35/741* (2013.01); *A61K 35/744* (2013.01); *A61K 38/05* (2013.01); *A61Q 11/00* (2013.01); *A61K 2035/115* (2013.01); *A61K 2800/74* (2013.01)

(58) Field of Classification Search
None
See application file for complete search history.

(56) References Cited

U.S. PATENT DOCUMENTS

| | | | | |
|---|---|---|---|---|
| 4,277,464 A * | 7/1981 | Reussner | ........... | A23G 4/14 |
| | | | | 424/49 |
| 2006/0018843 A1 | 1/2006 | Fine | | |
| 2008/0305151 A1* | 12/2008 | Sakai | ........... | A23L 2/39 |
| | | | | 424/439 |

FOREIGN PATENT DOCUMENTS

| | | | | |
|---|---|---|---|---|
| EP | 3086801 A1 * | 11/2016 | ........... | A61K 35/74 |
| GB | 2307476 | 5/1997 | | |
| JP | 2010124772 | 6/2010 | | |
| RU | WO-9420063 A2 * | 9/1994 | ........... | A61K 38/05 |
| WO | WO9420063 | 9/1994 | | |
| WO | WO1994020063 A2 * | 9/1994 | | |

OTHER PUBLICATIONS

Anonymous. "The 20 Amino Acids and Their Role in Protein Structures" http://www.proteinstructures.com/Structure/Structure/amino-acids.html (Year: 2010).*
Cerchietti et al. "Double-Blinded, Placebo-Controlled Trial on Intravenous L-Alanyl-L-Glutamine in the Incidence of Oral Mucositis Following Chemoradiotherapy in Patients with Head-and-Neck Cancer" Int. J. Radiation Oncology Biol. Phys. 65:1330-1337 (Year: 2006).*
Lee et al. "Cloning, Expression, and Characterization of Aminopeptidase P from the Hyperthermophilic Archaeon Thermococcus sp. Strain NA1" Appl. Environ. Microbiol. 72:1886-1890 (Year: 2006).*
Tao et al. "Salivary Antimicrobial Peptide Expression and Dental Caries Experience in Children" Antimicrobial Agents and Chemotherapy 49:3883-3888. (Year: 2005).*
H.S. Lee et al.: "Cloning Expression, and Characterization of Aminopeptidase P from the Hyperthermophilic Archaeon Thermococcus sp. Strain NA1", Applied and Environmental Microbiology, vol. 72, No. 3, Mar. 1, 2006, pp. 1886-1890.

* cited by examiner

*Primary Examiner* — James H Alstrum-Acevedo
*Assistant Examiner* — Zachary J Miknis

(57) ABSTRACT

The present invention provides an oral care composition comprising: (a) a dipeptide of the formula Xaa1-Xaa2 or Xaa2-Xaa1; wherein Xaa1 is an amino acid with a polar uncharged side chain; and Xaa2 is selected from an amino acid with a hydrophobic side chain, an amino acid with a polar uncharged side chain, and proline; or (b) a dipeptide of the formula Xaa3-Xaa4 or Xaa4-Xaa3; wherein Xaa3 is an amino acid with a hydrophobic side chain; and Xaa4 is selected from an amino acid with a hydrophobic side chain and an amino acid with a charged side chain.

12 Claims, No Drawings

PREBIOTIC ORAL CARE COMPOSITIONS CONTAINING AMINO ACIDS

BACKGROUND

The oral cavity contains many different species of bacteria. Some species of oral pathogenic bacteria (e.g. *Porphyromonas gingivalis, Tannerella forsythia* and *Aggregatibacter actinomycetemcomitans*) have been implicated in the development of periodontal diseases, such as periodontitis, gingivitis, necrotizing periodontitis, necrotizing gingivitis and peri-implantitis. Certain species of oral pathogenic bacteria have been implicated in tooth decay (e.g. *Streptococcus mutans*).

It is believed that certain species of oral bacteria are beneficial for maintaining the health of the periodontium. Without being bound by any theory, it is believed that these beneficial oral bacteria can interfere with colonization by pathogenic oral bacteria of the oral epithelium. For example, studies have shown that *Streptococcus sanguinis, Streptococcus mitis* and *Streptococcus salivarius* have inhibitory effects on *A. actinomycetemcomitans* colonization of epithelial cells in vitro (W. Teughels et al., J Dent Res 86(7), 611-617, 2007). It has also been shown, using a canine model, that the application of beneficial bacteria to periodontal pockets following root planing delays and reduces recolonization of the periodontal pockets by pathogenic bacteria (W. Teughels, et al., J Dent Res, 86(11), 1078-1082, 2007). The beneficial bacteria *Streptococcus sanguinis, Streptococcus mitis* and *Streptococcus salivarius* have also been shown to inhibit *A. actinomycetemcomitans*-induced production of the inflammatory cytokine interleukin-8 (IL-8) by the human oral keratinocyte cell line HOK-18A, which inflammatory response is implicated in periodontitis-related tissue destruction (I. Sliepen et al., J Dent Res 88(11), 1026-1030, 2009).

It is believed that selective stimulation of beneficial oral bacteria may provide a valid preventative approach for oral health, for example in the prevention of periodontitis.

BRIEF SUMMARY

In one aspect, the present invention provides an oral care composition comprising: (a) a dipeptide of the formula Xaa1-Xaa2 or Xaa2-Xaa1; wherein Xaa1 is an amino acid with a polar uncharged side chain; and Xaa2 is selected from an amino acid with a hydrophobic side chain, an amino acid with a polar uncharged side chain, and proline; or (b) a dipeptide of the formula Xaa3-Xaa4 or Xaa4-Xaa3; wherein Xaa3 is an amino acid with a hydrophobic side chain; and Xaa4 is selected from an amino acid with a hydrophobic side chain and an amino acid with a charged side chain.

Optionally, Xaa1, Xaa2, Xaa3 and Xaa4 are L-amino acids.

Optionally, the dipeptide is present in the composition in an amount of from 0.01 weight % to 10 weight %, based on the weight of the oral care composition.

Optionally, Xaa2 is an amino acid with an aliphatic hydrophobic side chain. Further optionally, Xaa2 is alanine, isoleucine, leucine or valine. Still further optionally, Xaa2 is leucine or valine.

Alternatively, Xaa2 is asparagine, cysteine, glutamine, methionine, serine or threonine. Optionally, Xaa2 is asparagine or glutamine.

Alternatively, Xaa2 is proline.

Optionally, Xaa1 is serine, methionine, threonine, cysteine, asparagine or glutamine. Further optionally, Xaa1 is serine. Alternatively, Xaa1 is methionine.

Optionally, Xaa3 is an amino acid with an aromatic hydrophobic side chain. Further optionally, Xaa3 is tryptophan, phenylalanine, or tyrosine. Still further optionally, Xaa3 is tryptophan. Alternatively, Xaa3 is phenylalanine.

Optionally, Xaa4 is aspartic acid, glutamic acid, arginine, histidine or lysine. Further optionally, Xaa4 is glutamic acid or histidine.

Alternatively, Xaa4 is an amino acid with an aliphatic hydrophobic side chain.

Optionally, Xaa4 is alanine, isoleucine, leucine or valine.

Optionally, the composition is a dentifrice, a toothpaste, a gel, a tooth powder, a mouthwash, a mouthrinse, a lozenge, a tablet, a spray, a gum, or a film.

Optionally, the composition further comprises at least one species of bacteria that has beneficial effects on oral health. Further optionally, the species of bacteria that has beneficial effects on oral health is selected from *Streptococcus mitis, Streptococcus salivarius, Streptococcus sanguinis, Actinomyces viscosus, Veillonella parvula, Streptococcus gordonii, Capnocytophaga sputigena, Actinomyces naeslundii* and combinations thereof.

In another aspect, the present invention provides an oral care composition of the present invention, for use in selectively promoting, in an oral cavity: growth, metabolic activity or colonization of bacteria that have beneficial effects on oral health, relative to growth, metabolic activity or colonization of pathogenic oral bacteria. In another aspect, the present invention provides an oral care composition of the present invention, for use in selectively promoting, in an oral cavity, biofilm formation by bacteria that have beneficial effects on oral health, relative to biofilm formation by pathogenic oral bacteria. In another aspect, the present invention provides an oral care composition of the present invention, for use in maintaining and/or re-establishing a healthy oral microbiota. In another aspect, the present invention provides an oral care composition of the present invention, for use in preventing one or more of gingivitis, periodontitis, peri-implantitis, peri-implant mucositis, necrotizing gingivitis, necrotizing periodontitis and caries.

In another aspect, the present invention provides a method of selectively promoting, in an oral cavity of a subject: growth, metabolic activity or colonization of bacteria that have beneficial effects on oral health, relative to growth, metabolic activity or colonization of pathogenic oral bacteria; the method comprising contacting the oral cavity with an oral care composition of the present invention. In another aspect, the present invention provides a method of selectively promoting, in an oral cavity of a subject, biofilm formation by bacteria that have beneficial effects on oral health, relative to biofilm formation by pathogenic oral bacteria; the method comprising contacting the oral cavity with an oral care composition of the present invention. The present invention also provides a method of maintaining and/or re-establishing a healthy oral microbiota in a subject, the method comprising contacting an oral cavity of the subject with an oral care composition of the present invention. The present invention also provides a method of preventing one or more of gingivitis, periodontitis, peri-implantitis, peri-implant mucositis, necrotizing gingivitis, necrotizing periodontitis and caries in a subject, the method comprising contacting an oral cavity of the subject with an oral care composition of the present invention.

In another aspect, the present invention provides the use, in an oral care composition, of (i) a dipeptide of the formula Xaa1-Xaa2 or Xaa2-Xaa1; wherein Xaa1 is an amino acid with a polar uncharged side chain; and Xaa2 is selected from an amino acid with a hydrophobic side chain, an amino acid with a polar uncharged side chain, and proline; or (ii) a dipeptide of the formula Xaa3-Xaa4 or Xaa4-Xaa3; wherein Xaa3 is an amino acid with a hydrophobic side chain; and Xaa4 is selected from an amino acid with a hydrophobic side chain and an amino acid with a charged side chain; to: (a) selectively promote growth, metabolic activity or colonization of bacteria that have beneficial effects on oral health, relative to growth, metabolic activity or colonization of pathogenic oral bacteria; (b) selectively promote biofilm formation by bacteria that have beneficial effects on oral health, relative to biofilm formation by pathogenic oral bacteria; (c) maintain and/or re-establish a healthy oral microbiota in a subject; or (d) prevent one or more of gingivitis, periodontitis, peri-implantitis, peri-implant mucositis, necrotizing gingivitis, necrotizing periodontitis and caries in a subject.

Optionally, the dipeptide selectively promotes growth, metabolic activity or colonization of bacteria that have beneficial effects on oral health, relative to growth, metabolic activity or colonization of pathogenic oral bacteria, after 24 hours incubation with the bacteria that have beneficial effects on oral health and the pathogenic oral bacteria.

Optionally, the dipeptide selectively promotes growth, metabolic activity or colonization of bacteria that have beneficial effects on oral health, relative to growth, metabolic activity or colonization of pathogenic oral bacteria, after 48 hours incubation with the bacteria that have beneficial effects on oral health and the pathogenic oral bacteria.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

As used herein, the expression "oral cavity" includes not only the cavity itself but also the saliva, teeth, gingiva, periodontal pockets, cheeks, tongue, mucosa, tonsils, any implants, and any device or structure which is placed into the oral cavity. The tonsils provide a reservoir (tonsil stones) for growth of anaerobic bacteria which may generate bad breath.

As used herein, the phrase "a healthy oral microbiota" refers to the microbial population of the oral cavity when the oral cavity is in a non-diseased state (for example, when there is no periodontal disease present, e.g. gingivitis, periodontitis, caries, peri-implantitis, peri-implant mucositis, necrotizing gingivitis and/or necrotizing periodontitis), i.e. a health-associated oral microbiota.

The term "beneficial bacteria" encompasses those bacteria which are present in the oral cavity in higher numbers or proportions in a healthy oral cavity, but which are present in lower numbers or proportions in conditions of oral disease (such as, for example, gingivitis, periodontitis, caries, peri-implantitis, peri-implant mucositis, necrotizing gingivitis and necrotizing periodontitis). This term also includes bacteria from oral or non-oral origins which have proven beneficial effects on oral health by preventing or treating oral diseases, which may be already present in the oral cavity or may be intentionally introduced into the oral cavity (for example as probiotics). Beneficial bacteria may, by their presence or metabolic activity, result in: lowering the number or proportion of pathogenic oral bacteria; lowering inflammation and inflammatory processes; lowering the metabolic activity of pathogenic species; lowering the production or inhibiting virulence factors produced by pathogenic bacteria; lowering or inhibiting biofilm formation; occupying a niche which may otherwise be colonized by pathogens; limiting a pathogen's ability to adhere to oral surfaces; affecting the viability, metabolic activity or growth of a pathogen; lowering the ability of a pathogen to produce virulence factors; degrading virulence factors produced by the pathogen or the oral microbiota; and/or attenuating the host response to pathogenic species. As discussed above, it is believed that these beneficial oral bacteria can interfere with colonization of the oral epithelium by pathogenic oral bacteria. It is believed that selective stimulation of beneficial oral bacteria may provide a valid preventative approach for oral health, for example in the prevention of periodontitis.

Bacteria require certain substrates in order to enable them to grow, multiply, be metabolically active and to colonize. Certain substrates can be used selectively by certain microorganisms (e.g. bacteria) to favor their growth, metabolic activity, multiplication and colonization, and thereby directly or indirectly suppress the growth of other microorganisms. The present inventors investigated the possibility of modifying the oral microbiota of a subject by selectively increasing the subject's indigenous beneficial oral bacterial population, by providing the beneficial oral bacteria with appropriate substrates for growth/multiplication.

Examples of beneficial bacteria include *Streptococcus mitis, Streptococcus salivarius, Streptococcus sanguinis, Actinomyces viscosus, Veillonella parvula, Streptococcus gordonii, Capnocytophaga sputigena* and *Actinomyces naeslundii*. Examples of pathogenic bacteria include *Streptococcus mutans, Prevotella intermedia, Porphyromonas gingivalis, Fusobacterium nucleatum, Tannerella forsythia, Aggregatibacter actinomycetemcomitans* and *Streptococcus sobrinus*.

The present inventors have found that certain dipeptides are able to cause an increase in growth, metabolic activity and biofilm formation of beneficial oral bacteria, while not causing an increase in growth, metabolic activity and biofilm formation of pathogenic oral bacteria.

The present invention therefore provides an oral care composition comprising: (a) a dipeptide of the formula Xaa1-Xaa2 or Xaa2-Xaa1; wherein Xaa1 is an amino acid with a polar uncharged side chain; and Xaa2 is selected from an amino acid with a hydrophobic side chain, an amino acid with a polar uncharged side chain, and proline; or (b) a dipeptide of the formula Xaa3-Xaa4 or Xaa4-Xaa3; wherein Xaa3 is an amino acid with a hydrophobic side chain; and Xaa4 is selected from an amino acid with a hydrophobic side chain and an amino acid with a charged side chain.

In some embodiments, Xaa1, Xaa2, Xaa3 and Xaa4 are L-amino acids.

In some embodiments, the amino acid Xaa1 (an amino acid with a polar uncharged side chain) is serine (Ser), methionine (Met), threonine (Thr), cysteine (Cys), asparagine (Asn) or glutamine (Gln). In certain embodiments, Xaa1 is serine or threonine. In other embodiments, Xaa1 is methionine or cysteine. In some embodiments, Xaa1 is serine. In other embodiments, Xaa1 is methionine.

When Xaa2 is an amino acid with a hydrophobic side chain, Xaa2 may in certain embodiments be an amino acid with an aliphatic hydrophobic side chain. In some of these embodiments, Xaa2 is alanine (Ala), isoleucine (Ile), leucine (Leu) or valine (Val). In certain embodiments, Xaa2 is leucine or valine. In certain embodiments, the dipeptide is Ser-Leu, Ser-Val, Leu-Ser or Val-Ser. In some embodiments, the dipeptide is Ser-Leu or Ser-Val.

When Xaa2 is an amino acid with a polar uncharged side chain, Xaa2 may in certain embodiments be asparagine (Asn), cysteine (Cys), glutamine (Gln), methionine (Met), serine (Ser) or threonine (Thr). In some of these embodiments, Xaa2 is asparagine or glutamine. In other embodiments, Xaa2 is cysteine or methionine. In other embodiments, Xaa2 is serine or threonine. In certain embodiments, the dipeptide is Ser-Asn, Ser-Gln, Asn-Ser or Gln-Ser. In some embodiments, the dipeptide is Ser-Asn or Ser-Gln.

In some embodiments, Xaa2 is proline (Pro). In one embodiment the dipeptide is Met-Pro.

In some embodiments, the amino acid Xaa3 (an amino acid with a hydrophobic side chain) is an amino acid with an aromatic hydrophobic side chain. In certain embodiments, Xaa3 is tryptophan (Trp), phenylalanine (Phe), or tyrosine (Tyr). In some embodiments, Xaa3 is tryptophan. In other embodiments, Xaa3 is phenylalanine.

When Xaa4 is an amino acid with a hydrophobic side chain, Xaa4 may in certain embodiments be an amino acid with an aliphatic hydrophobic side chain. In some of these embodiments, Xaa4 is alanine (Ala), isoleucine (Ile), leucine (Leu) or valine (Val). In certain embodiments, Xaa4 is leucine or valine. In certain embodiments, Xaa4 is leucine. In certain embodiments, the dipeptide is Trp-Leu or Leu-Trp.

When Xaa4 is an amino acid with a charged side chain, Xaa4 may in certain embodiments be aspartic acid (Asp), glutamic acid (Glu), arginine (Arg), histidine (His) or lysine (Lys). In certain embodiments, Xaa4 is aspartic acid or glutamic acid. In other embodiments, Xaa4 is arginine, histidine or lysine. In other embodiments, Xaa4 is glutamic acid or histidine. In some embodiments, the dipeptide is Trp-Glu, Trp-His, Glu-Trp, Glu-His, Phe-Glu or Glu-Phe. In some embodiments, the dipeptide is Glu-Trp, His-Trp or Phe-Glu. In some embodiments, the dipeptide is Phe-Glu.

In some embodiments, the dipeptide is Ser-Leu, Ser-Val, Ser-Asn, Ser-Gln, Met-Pro, Phe-Glu, Glu-Trp, Trp-Leu or His-Trp. In some embodiments, the dipeptide is Ser-Leu or Ser-Val. In other embodiments, the dipeptide is Ser-Asn, Ser-Gln, Met-Pro, Phe-Glu, Glu-Trp, Trp-Leu or His-Trp.

In some embodiments, the dipeptide is present in the composition in an amount of from 0.01 weight % to 10 weight %, from 0.05 weight % to 7.5 weight %, from 0.1 weight % to 5 weight %, or from 1 weight % to 2.5 weight %, based on the weight of the oral care composition.

In any of the above embodiments, the dipeptide may be present in the composition in an amount of from 1 µmol/ml to 50 µmol/ml, from 2.5 µmol/ml to 35 µmol/ml, from 5 µmol/ml to 25 µmol/ml, or from 10 µmol/ml to 20 µmol/ml. In certain embodiments, the dipeptide is present in the composition in an amount of 5 µmol/ml to 10 µmol/ml, or from 10 µmol/ml to 25 µmol/ml.

The oral care composition as described in any of the above embodiments may be a dentifrice, a toothpaste, a gel, a tooth powder, a mouthwash, a mouthrinse, a lozenge (which may be dissolvable or chewable), a tablet, a spray, a gum, or a film (which may be wholly or partially dissolvable, or indissolvable).

The oral care compositions as described in any of the above embodiments may further comprise at least one species of bacteria that has beneficial effects on oral health. In these embodiments, the composition may be referred to as a synbiotic composition, as it contains both a probiotic (the bacteria which has beneficial effects on oral health) and a prebiotic (the dipeptide which stimulates the growth, metabolic activity and/or colonization of the probiotic bacteria). In certain embodiments, the species of bacteria that has beneficial effects on oral health is selected from *Streptococcus mitis, Streptococcus salivarius, Streptococcus sanguinis, Actinomyces viscosus, Veillonella parvula, Streptococcus gordonii, Capnocytophaga sputigena, Actinomyces naeslundii* and combinations thereof.

The present invention also provides an oral care composition according to any of the above-described embodiments, for use in (a) selectively promoting, in an oral cavity: growth, metabolic activity or colonization of bacteria that have beneficial effects on oral health, relative to growth, metabolic activity or colonization of pathogenic oral bacteria; (b) selectively promoting, in an oral cavity, biofilm formation by bacteria that have beneficial effects on oral health, relative to biofilm formation by pathogenic oral bacteria; (c) maintaining and/or re-establishing a healthy oral microbiota; (d) preventing one or more of gingivitis, periodontitis, peri-implantitis, peri-implant mucositis, necrotizing gingivitis, necrotizing periodontitis and caries.

The present invention also provides for the use, in an oral care composition, of a dipeptide as described in any of the above embodiments to (a) selectively promote growth, metabolic activity or colonization of bacteria that have beneficial effects on oral health, relative to growth, metabolic activity or colonization of pathogenic oral bacteria; (b) selectively promote biofilm formation by bacteria that have beneficial effects on oral health, relative to biofilm formation by pathogenic oral bacteria; (c) maintain and/or re-establish a healthy oral microbiota in a subject; or (d) prevent one or more of gingivitis, periodontitis, peri-implantitis, peri-implant mucositis, necrotizing gingivitis, necrotizing periodontitis and caries in a subject.

The present invention also provides a method of (a) selectively promoting, in an oral cavity of a subject: growth, metabolic activity or colonization of bacteria that have beneficial effects on oral health, relative to growth, metabolic activity or colonization of pathogenic oral bacteria; (b) selectively promoting, in an oral cavity of a subject, biofilm formation by bacteria that have beneficial effects on oral health, relative to biofilm formation by pathogenic oral bacteria; (c) maintaining and/or re-establishing a healthy oral microbiota in a subject; or (d) preventing one or more of gingivitis, periodontitis, peri-implantitis, peri-implant mucositis, necrotizing gingivitis, necrotizing periodontitis and caries in a subject. Each of these methods comprises contacting an oral cavity of the subject with an oral care composition according to any of the above-described embodiments.

In the above methods, the subject may be a mammal. In some embodiments, the subject is a human. In some embodiments, the subject is an animal, for example a companion animal (e.g. a cat or dog).

In certain embodiments, the contacting of the oral cavity with the oral care composition comprises applying the oral care composition to the oral cavity using a brush, rinsing the oral cavity with the oral care composition in the form of a mouthwash, or spraying the oral care composition into the oral cavity using, for example, an atomizer.

In any of the above embodiments of the methods and uses, the bacteria that have beneficial effects of oral health may be selected from Streptococcus mitis, Streptococcus salivarius, Streptococcus sanguinis, Actinomyces viscosus, Veillonella parvula, Streptococcus gordonii, Capnocytophaga sputigena, Actinomyces naeslundii and combinations thereof. Additionally or alternatively, the pathogenic bacteria may be selected from Streptococcus mutans, Prevotella intermedia, Porphyromonas gingivalis, Fusobacterium nucleatum, Tannerella forsythia, Aggregatibacter actinomycetemcomitans, Streptococcus sobrinus and combinations thereof.

In any of the above embodiments wherein the methods and uses concern the selective promotion (in an oral cavity of a subject) of growth, metabolic activity or colonization of bacteria that have beneficial effects on oral health, relative to growth, metabolic activity or colonization of pathogenic oral bacteria, the bacteria that have beneficial effects of oral health may be selected from Streptococcus mitis, Streptococcus salivarius, Actinomyces viscosus, Veillonella parvula, Capnocytophaga sputigena and combinations thereof. Additionally or alternatively, the pathogenic bacteria may be selected from Streptococcus mutans, Prevotella intermedia, Porphyromonas gingivalis, Fusobacterium nucleatum, Tannerella forsythia, Aggregatibacter actinomycetemcomitans, Streptococcus sobrinus and combinations thereof, and in certain embodiments may be selected from Prevotella intermedia, Porphyromonas gingivalis, Fusobacterium nucleatum, Tannerella forsythia and combinations thereof.

In any of the above embodiments wherein the methods and uses concern the selective promotion of biofilm formation by bacteria that have beneficial effects on oral health, relative to biofilm formation by pathogenic oral bacteria, the pathogenic bacteria may be selected from Streptococcus mutans, Prevotella intermedia, Porphyromonas gingivalis, Fusobacterium nucleatum, Tannerella forsythia, Aggregatibacter actinomycetemcomitans and combinations thereof. Additionally or alternatively, the bacteria that have beneficial effects of oral health may be selected from Streptococcus sanguinis, Streptococcus gordonii and combinations thereof.

In some embodiments, the dipeptide selectively promotes growth, metabolic activity or colonization of bacteria that have beneficial effects on oral health, relative to growth, metabolic activity or colonization of pathogenic oral bacteria, after 24 hours incubation with the bacteria that have beneficial effects on oral health and the pathogenic oral bacteria.

In some embodiments, the dipeptide selectively promotes growth, metabolic activity or colonization of bacteria that have beneficial effects on oral health, relative to growth, metabolic activity or colonization of pathogenic oral bacteria, after 48 hours incubation with the bacteria that have beneficial effects on oral health and the pathogenic oral bacteria.

In the compositions of the present invention comprising dipeptides, the sequence of the amino acids of the dipeptide is reported from the N-terminal end (containing the free amino group) to the C-terminal end (containing the free carboxyl group). Therefore, for the example of "Ser-Val", the structure is as shown in Formula I; and, for "His-Trp", the structure is as shown in Formula II:

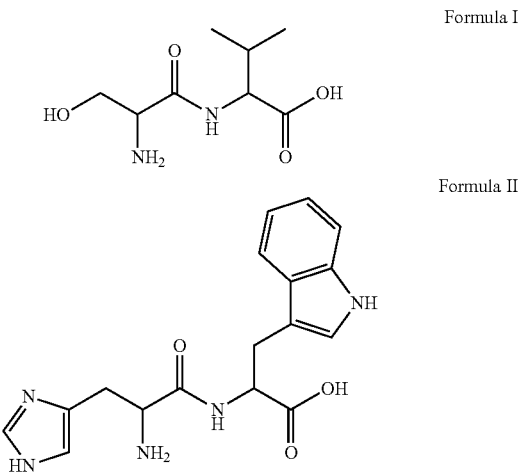

Formula I

Formula II

The oral care compositions of the present invention may further comprise additional ingredients. These additional ingredients may include, but are not limited to, abrasives, diluents, bicarbonate salts, pH modifying agents, surfactants, foam modulators, thickening agents, humectants, sweeteners, flavorants, pigments, antibacterial agents, anti-caries agents, anticalculus or tartar control agents, and mixtures thereof.

In some embodiments, particularly (but not limited to) those embodiments, wherein the oral care composition is a toothpaste, the compositions of the present invention may further comprise an abrasive. Abrasives that may be used include silica abrasives such as precipitated or hydrated silicas having a mean particle size of up to about 20 microns, such as Zeodent 105 and Zeodent 114 marketed by J.M. Huber Chemicals Division, Havre de Grace, Md. 21078, or Sylodent 783 marketed by Davison Chemical Division of W.R. Grace & Company. Abrasives such as Sorbosil AC 43 from PQ Corporation may also be included. Other useful dentifrice abrasives include aluminium oxide, aluminum silicate, calcined alumina, bentonite or other siliceous materials, insoluble phosphates, and mixtures thereof. The abrasive may be present in an amount of from 5 to 30 wt % based on the weight of the composition, optionally from 10 to 20 wt % based on the weight of the composition. In certain embodiments, particularly (but not limited to) those embodiments wherein the oral care composition is a mouthwash or mouthrinse, the compositions may be free of abrasives.

In some embodiments, the oral care compositions of the present invention comprise at least one bicarbonate salt useful for example to impart a "clean feel" to teeth and gums due to effervescence and release of carbon dioxide. Any orally acceptable bicarbonate can be used, including without limitation, alkali metal bicarbonates such as sodium and potassium bicarbonates, ammonium bicarbonate and the like. The one or more additional bicarbonate salts are optionally present in a total amount of about 0.1 wt. % to about 50 wt. %, for example about 1 wt. % to 20 wt. %, by total weight of the composition.

In some embodiments, the oral care compositions of the present invention comprise at least one pH modifying agent. Such agents include acidifying agents to lower pH, basifying agents to raise pH, and buffering agents to control pH within a desired range. For example, one or more compounds selected from acidifying, basifying and buffering agents can be included to provide a pH of 2 to 10, or in various illustrative embodiments, 2 to 8, 3 to 9, 4 to 8, 5 to 7, 6 to 10, 7 to 9, etc. Any orally acceptable pH modifying agent can be used, including without limitation, carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate), imidazole and the like. One or more pH modifying agents are optionally present in a total amount effective to maintain the composition in an orally acceptable pH range.

The oral care compositions of the invention may also comprise at least one surfactant. Any orally acceptable surfactant, most of which are anionic, nonionic or amphoteric, can be used. Suitable anionic surfactants include without limitation, water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium coconut monoglyceride sulfonate, sodium lauryl sarcosinate, sodium lauryl isoethionate, sodium laureth carboxylate and sodium dodecyl benzenesulfonate. Suitable nonionic surfactants include without limitation, poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include without limitation, derivatives of $C_{8-20}$ aliphatic secondary and tertiary amines having an anionic group such as carboxylate, sulfate, sulfonate, phosphate or phosphonate. Betaines may also be used, a suitable example of which is cocoamidopropyl betaine. One or more surfactants are optionally present in a total amount of about 0.01 wt. % to about 10 wt. %, for example, from about 0.05 wt. % to about 5 wt. %, or from about 0.1 wt. % to about 2 wt. % by total weight of the composition.

The oral care compositions of the invention may comprise at least one foam modulator, useful for example to increase amount, thickness or stability of foam generated by the composition upon agitation. Any orally acceptable foam modulator can be used, including without limitation, polyethylene glycols (PEGs), also known as polyoxyethylenes. High molecular weight PEGs are suitable, including those having an average molecular weight of 200,000 to 7,000,000, for example 500,000 to 5,000,000, or 1,000,000 to 2,500,000. One or more PEGs are optionally present in a total amount of about 0.1 wt. % to about 10 wt. %, for example from about 0.2 wt. % to about 5 wt. %, or from about 0.25 wt. % to about 2 wt. %, by total weight of the composition.

The oral care compositions of the present invention may comprise at least one thickening agent, useful for example to impart a desired consistency and/or mouth feel to the composition. Any orally acceptable thickening agent can be used, including without limitation, carbomers, also known as carboxyvinyl polymers, carrageenans, also known as Irish moss and more particularly t-carrageenan (iota-carrageenan), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, colloidal silica and the like. A preferred class of thickening or gelling agents includes a class of homopolymers of acrylic acid crosslinked with an alkyl ether of pentaerythritol or an alkyl ether of sucrose, or carbomers. Carbomers are commercially available from B. F. Goodrich as the Carbopol® series. Particularly preferred Carbopols include Carbopol 934, 940, 941, 956, 974P, and mixtures thereof. Silica thickeners such as DT 267 (from PPG Industries) may also be used. One or more thickening agents are optionally present in a total amount of from about 0.01 wt. % to 15 wt. %, for example from about 0.1 wt. % to about 10 wt. %, or from about 0.2 wt. % to about 5 wt. %, by total weight of the composition.

The compositions of the invention may comprise at least one viscosity modifier, useful for example to help inhibit settling or separation of ingredients or to promote re-dispersibility upon agitation of a liquid composition. Any orally acceptable viscosity modifier can be used, including without limitation, mineral oil, petrolatum, clays and organomodified clays, silica and the like. One or more viscosity modifiers are optionally present in a total amount of from about 0.01 wt. % to about 10 wt. %, for example, from about 0.1 wt. % to about 5 wt. %, by total weight of the composition.

The compositions of the invention may also comprise at least one humectant. Any orally acceptable humectant can be used, including without limitation, polyhydric alcohols such as glycerin, sorbitol (optionally as a 70 wt. % solution in water), xylitol or low molecular weight polyethylene glycols (PEGs). Most humectants also function as sweeteners. One or more humectants are optionally present in a total amount of from about 1 wt. % to about 70 wt. %, for example, from about 1 wt. % to about 50 wt. %, from about 2 wt. % to about 25 wt. %, or from about 5 wt. % to about 15 wt. %, by total weight of the composition.

The oral care compositions of the present invention may comprise at least one sweetener, useful for example to enhance taste of the composition. One or more sweeteners are optionally present in a total amount depending strongly on the particular sweetener(s) selected, but typically 0.005 wt. % to 5 wt. %, by total weight of the composition, optionally 0.005 wt. % to 0.2 wt. %, further optionally 0.05 wt. % to 0.1 wt. % by total weight of the composition.

The compositions of the present invention may also comprise at least one flavorant, useful for example to enhance taste of the composition. Any orally acceptable natural or synthetic flavorant can be used, including without limitation tea flavours, vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants and the like. Also encompassed within flavorants herein are ingredients that provide fragrance and/or other sensory effect in the mouth, including cooling or warming effects. Such ingredients illustratively include menthol, menthyl acetate, menthyl lactate, camphor, eucalyptus oil, eucalyptol, anethole, eugenol, cassia, oxanone, α-irisone, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthone glycerol acetal (MGA) and the like. One or more flavorants are optionally present in a total amount of from about 0.01 wt. % to about 5 wt. %, for example, from about 0.03 wt. % to about 2.5 wt. %, optionally about 0.05 wt. % to about 1.5 wt. %, further optionally about 0.1 wt. % to about 0.3 wt. % by total weight of the composition.

The compositions of the invention may comprise at least one colorant. Colorants herein include pigments, dyes, lakes and agents imparting a particular luster or reflectivity such as pearling agents. Any orally acceptable colorant can be used, including without limitation talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride, and the like. One or more colorants are optionally present in a total amount of from about 0.001 wt. % to about 20 wt. %, for example, from about 0.01 wt. % to about 10 wt. %, or from about 0.1 wt. % to about 5 wt. %, by total weight of the composition.

The compositions of the present invention may also comprise an antibacterial or preservative agent, such as chlorhexidine, triclosan, quaternary ammonium compounds (for example benzalkonium chloride) or parabens such as methylparaben or propylparaben. One or more antibacterial or preservative agent is optionally present in the composition in a total amount of from about 0.01 wt. % to about 0.5 wt. %, optionally about 0.05 wt. % to about 0.1 wt. % by total weight of the composition.

The oral care compositions may also comprise a fluoride ion source. Fluoride ion sources include, but are not limited to: stannous fluoride, sodium fluoride, potassium fluoride, potassium monofluorophosphate, sodium monofluorophosphate, ammonium monofluorophosphate, sodium fluorosilicate, ammonium fluorosilicate, amine fluoride such as olaflur (N'-octadecyltrimethylendiamine-N,N,N'-tris(2-ethanol)-dihydrofluoride), ammonium fluoride, and combinations thereof. In certain embodiments the fluoride ion source includes stannous fluoride, sodium fluoride, amine fluorides, sodium monofluorophosphate, as well as mixtures thereof. In certain embodiments, the oral care composition of the invention may also contain a source of fluoride ions or fluorine-providing ingredient in amounts sufficient to supply about 50 to about 5000 ppm fluoride ion, e.g., from about 100 to about 1000, from about 200 to about 500, or about 250 ppm fluoride ion. Fluoride ion sources may be added to the compositions of the invention at a level of about 0.001 wt. % to about 10 wt. %, e.g., from about 0.003 wt. % to about 5 wt. %, 0.01 wt. % to about 1 wt., or about 0.05 wt. %. However, it is to be understood that the weights of fluoride salts to provide the appropriate level of fluoride ion will obviously vary based on the weight of the counter ion in the salt, and one of skill in the art may readily determine such amounts. A preferred fluoride salt may be sodium fluoride.

The compositions of the present invention may comprise a saliva stimulating agent useful, for example, in amelioration of dry mouth. Any orally acceptable saliva stimulating agent can be used, including without limitation food acids such as citric, lactic, malic, succinic, ascorbic, adipic, fumaric and tartaric acids, and mixtures thereof. One or more saliva stimulating agents are optionally present in saliva stimulating effective total amount.

The compositions of the present invention may include antisensitivity agents, e.g., potassium salts such as potassium nitrate, potassium bicarbonate, potassium chloride, potassium citrate, and potassium oxalate; capsaicin; eugenol; strontium salts; chloride salts and combinations thereof. Such agents may be added in effective amounts, e.g., from about 1 wt. % to about 20 wt. % by weight based on the total weight of the composition, depending on the agent chosen.

The composition of the invention may further comprise an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

The compositions of the present invention may additionally optionally comprise a tartar control (anticalculus) agent as provided below. Tartar control agents among those useful herein include salts of the specified agents, including alkali metal and ammonium salts. The agents include: phosphates and polyphosphates, polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, sodium trimetaphosphate, sodium hexametaphosphate and mixtures thereof. Other useful tartar control agents include polycarboxylate polymers and polyvinyl methyl ether/maleic anhydride (PVM/MA) copolymers, such as GANTREZ®.

EXAMPLES

Example 1

The metabolic activity of various beneficial oral bacteria and pathogenic oral bacteria in the presence of the dipeptides Ser-Leu, Ser-Val, Ser-Asn, Ser-Gln, Met-Pro, Phe-Glu, Glu-Trp, Trp-Leu or His-Trp was investigated. In the examples, the amino acid residues present in the dipeptides are L-amino acid residues.

The beneficial oral bacteria tested were *Streptococcus mitis, Streptococcus salivarius, Streptococcus sanguinis, Actinomyces viscosus, Streptococcus gordonii, Capnocytophaga sputigena, Actinomyces naeslundii* and *Veillonella parvula*. The pathogenic oral bacteria tested were *Streptococcus mutans, Prevotella intermedia, Porphyromonas gingivalis, Fusobacterium nucleatum, Tannerella forsythia, Aggregatibacter actinomycetemcomitans* and *Streptococcus sobrinus*.

Substrates that were able to increase the metabolic activity of at least one of the above beneficial bacteria while not or only minimally increasing the growth of the pathogenic bacteria are considered to be prebiotic substrates.

The extent of metabolic activity of the tested bacteria in the presence of the above-mentioned dipeptides after 24 hours and 48 hours was investigated through a high throughput phenotype microarray system (PM) for microbial cells (Biolog Inc.). Each PM can contain up to 95 different biochemical compounds (e.g. di-peptides) that may act as substrates for bacteria as well as one negative control, not containing the substrates. Microarray plates were used in which the different wells of each plate were pre-loaded (by the manufacturer, Biolog Inc.) with different di-peptides to be tested. Each bacterial species was tested using a separate microarray plate. Thus, a single bacterial species was tested with a variety of dipeptides on each particular plate. The microarrays are based on redox technology, using cell respiration as a universal reporter. Active cell respiration results in the reduction of a tetrazolium dye and in the formation of a strong color—for example, when using the tetrazolium dye "Biolog Redox Dye Mix D", the color changes from transparent/colourless to purple when the dye is reduced. The observation of this color change indicates which of the substrates improve the metabolic activity and health of the cells.

Each bacterial species was collected from blood agar plates (incubated for 48 hours anaerobically at 37° C.) and transferred to an IF-0 Base inoculation fluid (Biolog Inc.), which is a nutritionally poor medium. The resulting cell suspension was adjusted to a transmittance of 42% (relative to the transmittance of the base inoculation fluid with no bacterial species present) at 492 nm using a BioRad Smart-Spec 3000 Photometer (the adjustment being effected by adding either further inoculation fluid or further bacteria until the transmittance of 42% was achieved). A 1:5 dilution of this suspension was prepared by mixing 3 mL of the 42% transmittance cell suspension with 15 mL of an inoculation fluid (which inoculation fluid was formed by mixing 11.6 mL sterile water, 62.5 mL IF-0 base inoculation fluid and 0.9 mL of the tetrazolium dye "Biolog Redox Dye mix D"), resulting in a final cell density which was equal to 85% transmittance using a BioRad SmartSpec 3000 Photometer. 680 µL of a 2M sodium succinate/200 µM ferric citrate solution in distilled water was added to 68 mL of the 85% transmittance cell suspension and 100 µL of this mixture was added to each well (the various di-peptides being already present in powder form in the relevant wells of the plate as obtained from the supplier i.e. Biolog Inc.).

All plates were incubated in an anaerobic atmosphere at 37° C. Color changes were measured spectrophotometrically at 492 nm (Thermo Scientific Multiskan Ascent) at 24 hrs and 48 hrs using the same plate at both time points. For each bacterium tested, a respective control was also used, the control being a well of the plate which contained the particular bacterium (cell suspension) but did not contain any dipeptide. After 24 hrs and 48 hrs under continuous shaking in a Multiscan microplate reader, the optical density (OD) of the synthetic medium at 24 hours and 48 hours was measured (using the microplate reader) at a wavelength of 492 nm for each combination of bacterium/dipeptide, and for each of their respective controls (i.e. which contained the particular bacterium but no dipeptide). For each bacterium, the OD value obtained at 24 hrs and at 48 hrs was divided by the OD value obtained for the respective control at 24 hrs and 48 hrs (respectively), so that the control had a value of 1. A value greater than 1 for a particular combination of bacterium with dipeptide therefore indicates that the increase in metabolic activity of the bacteria after 24 hrs or 48 hrs was greater than the increase observed for the control.

The experiment was carried out three times for each combination of bacterium with dipeptide, with each repeat being carried out on a different day (thus providing three biological replicas). The controls were also carried out three times, as above. The values shown are the average (mean) of the three single values obtained (as detailed above) for each combination of bacterium with dipeptide, at 24 hrs and at 48 hrs. The results are shown in Tables 1 to 4, below:

TABLE 1

Pathogenic bacteria at 24 hrs

|  | A actino** | F nucleatu | P gingivalis | P intermedi | T forsythia | S mutans | S sobrinus |
|---|---|---|---|---|---|---|---|
| Ser-Leu | 1.6871 | 1.4813 | 1.4626 | 1.5403 | 1.3950 | 1.6244 | 1.4887 |
| Ser-Val | 1.4527 | 1.3741 | 1.3880 | 1.4709 | 1.2842 | 1.4622 | 1.3133 |
| Met-Pro | 0.9162 | 0.8752 | 1.0029 | 0.9704 | 0.9040 | 0.9563 | 1.0338 |
| Phe-Glu | 0.9204 | 0.9451 | 0.9806 | 1.0519 | 1.0452 | 1.0352 | 1.0354 |
| Ser-Asn | 1.3093 | 1.2165 | 1.0079 | 1.1002 | 1.2030 | 1.2715 | 1.2753 |
| Ser-Gln | 0.9996 | 1.2502 | 1.1453 | 1.2382 | 1.1929 | 1.2511 | 1.1504 |
| Glu-Trp | 0.9494 | 0.9011 | 0.9385 | 1.0170 | 0.9320 | 0.9492 | 1.0018 |
| Trp-Leu | 1.0357 | 0.9945 | 1.0236 | 1.0663 | 1.0234 | 1.0145 | 1.1681 |
| His-Trp | 0.9439 | 0.9185 | 1.0126 | 1.0278 | 0.8973 | 1.0292 | 1.0811 |

**A actinomycetemcomitans

TABLE 2

Beneficial bacteria at 24 hrs

|  | A naeslundi | C sputigena | S gordonii | A viscosus | S salivarius | S sanguinis | V parvula | S mitis |
|---|---|---|---|---|---|---|---|---|
| Ser-Leu | 1.4949 | 1.9645 | 1.5333 | 2.2523 | 1.4865 | 1.2625 | 1.4153 | 1.6052 |
| Ser-Val | 1.4073 | 1.4541 | 1.4328 | 2.1120 | 1.3826 | 1.2030 | 1.2776 | 1.4166 |
| Met-Pro | 1.0381 | 2.5077 | 1.0870 | 1.5865 | 0.9990 | 0.8599 | 0.7714 | 1.0020 |
| Phe-Glu | 0.9642 | 2.1428 | 0.8472 | 1.3824 | 1.0411 | 1.0204 | 0.8043 | 1.0644 |
| Ser-Asn | 1.3199 | 2.2418 | 0.8814 | 1.7174 | 1.1917 | 1.1935 | 1.1101 | 1.0807 |
| Ser-Gln | 1.2183 | 2.2409 | 0.9754 | 1.6173 | 1.1847 | 1.1901 | 0.8812 | 1.0595 |
| Glu-Trp | 1.1008 | 1.7818 | 1.1537 | 1.5845 | 1.0068 | 0.9983 | 0.8378 | 0.9457 |
| Trp-Leu | 1.1778 | 0.8565 | 1.2109 | 1.6496 | 1.0960 | 0.9310 | 0.8734 | 1.0445 |
| His-Trp | 1.3153 | 1.3266 | 1.0431 | 1.8735 | 0.9767 | 1.0228 | 1.1364 | 0.9734 |

TABLE 3

Pathogenic bacteria at 48 hrs

|  | A actino** | F nucleatu | P gingivalis | P intermedi | T forsythia | S mutans | S sobrinus |
|---|---|---|---|---|---|---|---|
| Ser-Leu | 2.2912 | 1.7358 | 1.8440 | 1.8484 | 1.8466 | 2.2977 | 2.0704 |
| Ser-Val | 1.9697 | 1.5983 | 1.9267 | 1.7953 | 1.7260 | 2.0721 | 1.8354 |
| Met-Pro | 0.8616 | 0.8113 | 1.0774 | 0.9393 | 0.9403 | 0.9242 | 1.0538 |
| Phe-Glu | 0.9345 | 0.9112 | 0.9029 | 0.9562 | 1.0015 | 0.9816 | 1.0539 |
| Ser-Asn | 1.7285 | 1.4289 | 1.2165 | 1.1329 | 1.4354 | 1.7588 | 1.7028 |
| Ser-Gln | 1.1574 | 1.6185 | 1.4999 | 1.3661 | 1.4647 | 1.7642 | 1.6280 |
| Glu-Trp | 0.8665 | 0.8364 | 0.8770 | 0.9148 | 0.9303 | 1.0170 | 0.9874 |
| Trp-Leu | 1.1455 | 1.0254 | 1.2127 | 1.0399 | 1.1079 | 1.1337 | 1.2761 |
| His-Trp | 0.9818 | 0.9774 | 1.3518 | 1.2057 | 0.9897 | 1.5031 | 1.2074 |

**A actinomycetemcomitans

TABLE 4

Beneficial bacteria at 48 hrs

|  | A naeslundi | C sputigena | S gordonii | A viscosus | S salivarius | S sanguinis | V parvula | S mitis |
|---|---|---|---|---|---|---|---|---|
| Ser-Leu | 1.8831 | 1.6522 | 1.8912 | 2.5540 | 2.0833 | 1.6049 | 1.4281 | 2.0461 |
| Ser-Val | 1.7338 | 1.4933 | 1.7640 | 2.4349 | 1.9626 | 1.5280 | 1.3095 | 1.8051 |
| Met-Pro | 1.0427 | 1.8376 | 1.0447 | 2.0588 | 0.9500 | 0.8295 | 0.6345 | 0.9214 |
| Phe-Glu | 0.9466 | 1.7139 | 0.9890 | 2.1224 | 0.9959 | 1.0208 | 0.7552 | 1.1176 |
| Ser-Asn | 1.6167 | 1.5699 | 1.3337 | 2.0421 | 1.5886 | 1.5794 | 1.1143 | 1.5785 |
| Ser-Gln | 1.5857 | 1.6963 | 1.4584 | 2.0308 | 1.6185 | 1.6298 | 0.8706 | 1.5980 |
| Glu-Trp | 1.2040 | 1.4150 | 1.4320 | 2.1016 | 0.9525 | 1.0200 | 0.7873 | 0.9396 |
| Trp-Leu | 1.4354 | 0.9454 | 1.2858 | 2.0774 | 1.1505 | 0.9561 | 0.7918 | 1.0524 |
| His-Trp | 1.5439 | 1.3068 | 1.1070 | 2.2797 | 1.0689 | 1.0830 | 1.4269 | 1.0242 |

In the above data, a value of 2 was taken as the threshold above which the dipeptide caused markedly increased metabolic activity of the bacterium. This value was selected in order to exclude low-stimulating metabolites and avoid false positive results.

As can be seen from the above data, Ser-Leu, Ser-Val, Met-Pro, Phe-Glu, Ser-Asn and Ser-Gln exhibited prebiotic effects at 24 hrs, and Met-Pro, Phe-Glu, Ser-Asn, Ser-Gln, Glu-Trp, Trp-Leu and His-Trp exhibited prebiotic effects at 48 hrs. Without being bound by any theory, it is believed that those substrates which exhibit prebiotic effects at 48 hrs may provide beneficial effects to the oral cavity upon prolonged use.

As Ser-Leu and Ser-Val are metabolized faster by the beneficial bacteria than by the pathogenic bacteria (shown by a value of 2 in the above data sets being reached at 24 hrs for the beneficial bacteria but not for the pathogenic bacteria), the presence of Ser-Leu or Ser-Val would be expected to cause the beneficial bacteria to suppress the growth of the pathogenic bacteria within a short timescale, thus maintaining a healthy oral microbiota. As Ser-Leu and Ser-Val are metabolized faster by the beneficial bacteria than by the pathogenic bacteria, these dipeptides are consumed/metabolized (and thus taken out of the environment) by the beneficial bacteria before the pathogenic bacteria can start using them. Without being bound by any theory, it is believed that the stimulatory effect of Ser-Leu and Ser-Val on the pathogenic bacteria as seen at 48 hrs might be abolished when a mixture of beneficial and pathogenic bacteria is present (such as in the oral cavity), as the dipeptide substrates have already been metabolized by the beneficial bacteria and are therefore unavailable for use by the pathogenic bacteria. Thus, if the growth/metabolic activity/colonization of the beneficial bacteria is stimulated before that of the pathogenic bacteria, then the beneficial bacteria can multiply and exert an inhibitory effect on the pathogenic bacteria before the latter have the chance to grow/multiply.

Example 2

The extent of growth of various beneficial oral and pathogenic oral bacteria in the presence of the dipeptides Met-Pro and Phe-Glu, as examples, was investigated. The amino acid residues present in the dipeptides are L-amino acid residues.

The beneficial oral bacteria tested were Streptococcus mitis, Streptococcus salivarius, Streptococcus sanguinis, Actinomyces viscosus, Streptococcus gordonii, Capnocytophaga sputigena, Actinomyces naeslundii and Veillonella parvula. The pathogenic oral bacteria tested were Streptococcus mutans, Prevotella intermedia, Porphyromonas gingivalis, Fusobacterium nucleatum, Tannerella forsythia, Aggregatibacter actinomycetemcomitans and Streptococcus sobrinus.

Substrates that were able to increase the growth (or maximal growth density or extent of growth) of at least one of the above beneficial bacteria while not or only minimally increasing the growth (or maximal growth density) of the pathogenic bacteria are considered to be prebiotic compounds.

The extent of growth of the tested bacteria in response to selected compounds (Met-Pro, Phe-Glu) was investigated by setting up growth curves in a nutritionally rich medium (brain heart infusion broth (BHI), Oxoid), over 48 hours. Late exponential growth phase liquid cultures were prepared by transferring the respective bacterium from blood agar plates to BHI and overnight incubation at 37° C. in an anaerobic atmosphere for A. viscosus, V. parvula, F. nucleatum, P. gingivalis, P. intermedia, T. forsythia, A. naeslundii, and C. sputigena, and in a 5% $CO_2$ environment for S. salivarius, S. sanguinis, S. mitis, A. actinomycetemcomitans, S. mutans, S. sobrinus and S. gordonii. Overnight cultures were transferred to BHI and adjusted to a concentration of $1\times10^7$ CFU/ml (colony forming units per ml) by measuring the optical density at 600 nm ($OD_{600}$) (BioRad SmartSpec 3000). For each strain, 200 μl of the bacterial suspension was added to a 96-well plate containing 20 μl of the respective di-peptides. Final concentrations of the di-peptides were set to 5, 10, 20 and 25 μmol/ml. For each bacterium tested, a respective control was also used, which did not contain the dipeptide. Plates were incubated as previously described.

For each combination of bacterium/dipeptide, and for each of their respective controls (i.e. the particular bacterium in the nutritionally rich medium with no dipeptide), the optical density was measured at 630 nm ($OD_{630}$) at 0 h, 24 h and 48 h (Thermo Scientific Multiskan Ascent). Additionally, the $OD_{630}$ for combinations of bacterium/dipeptide grown in a 5% $CO_2$ environment were also measured every hour between 0 h and 9 h. For each combination of bacterium/dipeptide, the maximal OD value obtained over the 48 hr time period was divided by the maximal OD value obtained for the respective control over the 48 hr period, so that the control had a value of 1. A value greater than 1 for a particular combination of bacterium with dipeptide therefore indicates that the extent of bacterial growth over 48 hrs was greater than extent of bacterial growth over 48 hrs for the control.

The experiment was carried out on three different days (thus providing 3 biological replicas) and on each day the experiment was carried out in quadruple (thus providing 4 technical replicas) for each combination of bacterium with dipeptide and for each control. For each day and for each combination, the average (mean) of the values obtained (as detailed above) for the four technical replicas was calculated to provide a single value for each combination on each day. The values shown in Tables 5 to 6, below, are the average (mean) of the three single values obtained for each combination of bacterium with dipeptide. The results are shown in Tables 5 to 6, below:

In the above data, a value of 1.25 was taken as the threshold above which the dipeptide caused markedly increased extent of growth of the bacterium relative to the control. This value was selected in order to exclude low-stimulating metabolites and avoid false positive results.

As can be seen from the above data, Phe-Glu, exhibited prebiotic effects at concentrations of 5 and 10 μmol/ml, and Met-Pro, exhibited prebiotic effects at concentrations of 25, 20 and 10 μmol/ml.

Example 3

The effects of the dipeptides Met-Pro and Phe-Glu, as examples, upon biofilm growth of various beneficial oral bacteria and pathogenic oral bacteria was also investigated. The amino acid residues present in the dipeptides are L-amino acid residues.

Substrates that were able to increase the biofilm mass of at least one of the above beneficial bacteria while not or only minimally increasing the biofilm mass of the pathogenic bacteria are considered to be prebiotic compounds.

The increase in biofilm formation of the tested bacteria in response to selected compounds (Met-Pro, Phe-Glu) was investigated by setting up biofilm growth assays in a nutritionally rich medium (brain heart infusion broth (BHI), Oxoid), over 48 hours. Late exponential growth phase liquid cultures were prepared by transferring the respective bacterium from blood agar plates to BHI and overnight incubation at 37° C. in an anaerobic atmosphere for A. viscosus, V. parvula, F. nucleatum, P. gingivalis, P. intermedia, T. forsythia, A. naeslundii, and C. sputigena, and in a 5% $CO_2$ environment for S. salivarius, S. sanguinis, S. mitis, A. actinomycetemcomitans, S. mutans, and S. gordonii. Overnight cultures were transferred to BHI and adjusted to a concentration of $1\times10^7$ CFU/ml by measuring the optical density at 600 nm ($OD_{600}$) (BioRad SmartSpec 3000). For each strain, 200 μl of the bacterial suspension was added to a 96-well plate containing 20 μl of the respective di-peptides. Final concentrations of the di-peptides were set to

TABLE 5

Pathogenic bacteria over 48 hours

|  | Phe-Glu 25 μmol/ml | Phe-Glu 20 μmol/ml | Phe-Glu 10 μmol/ml | Phe-Glu 5 μmol/ml | Met-Pro 25 μmol/ml | Met-Pro 20 μmol/ml | Met-Pro 10 μmol/ml | Met-Pro 5 μmol/ml |
|---|---|---|---|---|---|---|---|---|
| A actino* | 0.2320 | 0.2201 | 0.3227 | 0.5643 | 0.2297 | 0.3282 | 0.6321 | 0.7454 |
| F nucleatum | 0.2402 | 0.2311 | 0.8493 | 0.7990 | 0.7273 | 0.7782 | 0.8667 | 0.8422 |
| P gingivalis | 0.4208 | 0.4181 | 0.9810 | 0.8526 | 0.4276 | 0.7021 | 0.8266 | 0.8702 |
| P intermedia | 0.2224 | 0.2094 | 0.2856 | 1.1149 | 0.2336 | 0.3193 | 0.9742 | 0.9177 |
| S mutans | 0.2492 | 0.4212 | 0.9003 | 0.9703 | 0.5618 | 0.7929 | 0.9083 | 0.9473 |
| S sobrinus | 0.4315 | 0.5832 | 0.9900 | 1.0790 | 0.8547 | 1.0167 | 1.0301 | 0.9294 |
| T forsythia | 0.8302 | 0.7707 | 0.7490 | 1.0118 | 0.7018 | 0.7533 | 0.9743 | 0.9244 |

*A actinomycetemcomitans

TABLE 6

Beneficial bacteria over 48 hours

|  | Phe-Glu 25 μmol/ml | Phe-Glu 20 μmol/ml | Phe-Glu 10 μmol/ml | Phe-Glu 5 μmol/ml | Met-Pro 25 μmol/ml | Met-Pro 20 μmol/ml | Met-Pro 10 μmol/ml | Met-Pro 5 μmol/ml |
|---|---|---|---|---|---|---|---|---|
| A naeslundii | 0.1653 | 0.1648 | 0.4962 | 0.7791 | 0.3360 | 0.5466 | 0.8131 | 0.8420 |
| C sputigena | 1.1804 | 1.0801 | 0.9872 | 0.9921 | 0.9701 | 2.9796 | 3.5579 | 0.9618 |
| S gordonii | 0.2908 | 0.3992 | 0.8613 | 0.9682 | 0.6853 | 0.7735 | 0.9528 | 0.9757 |
| A viscosus | 0.1563 | 0.1598 | 0.3845 | 0.5112 | 0.2498 | 0.3154 | 0.4102 | 0.4873 |
| S salivarius | 0.2322 | 0.2953 | 0.8123 | 0.9916 | 0.5262 | 0.7572 | 1.0153 | 0.9729 |
| S sanguinis | 0.2334 | 0.2451 | 0.5644 | 0.8140 | 0.5011 | 0.6852 | 0.9070 | 0.9059 |
| V parvula | 1.0475 | 0.9533 | 1.0199 | 1.0286 | 0.9671 | 0.9516 | 0.9808 | 0.9980 |
| S mitis | 0.4367 | 0.3250 | 2.0642 | 1.9957 | 1.7501 | 1.8922 | 1.2332 | 0.9134 |

5, 10, 20 and 25 μmol/ml. For each bacterium tested, a respective control was also used, which did not contain the dipeptide. Additionally, for each bacterium tested, a background control, to correct for background staining, was added. This background control contained the bacterium tested and 0.03 weight % chlorhexidine, as an antiseptic. Plates were incubated as previously described. After 48 hrs the supernatant was removed from the wells of the plates. The wells were washed twice with 1×100 μL PBS (phosphate buffered saline), fixed for 20 minutes with 96% vol. ethanol (96% vol. solution in water) and the biofilm retained at the bottom of the wells was stained with 1 weight % crystal violet (1 weight % solution in water). The bound dye was dissolved with 5% vol. acetic acid (5% vol. solution in water). Quantification of the stained biofilm was performed by measuring the absorbance at 630 nm using a Multiskan Ascent microplate reader (Thermo Scientific).

For each combination of bacterium/dipeptide, the OD value obtained at 48 hrs was divided by the OD value obtained for the respective control after subtracting the OD value of the background control, so that the control had a value of 1. A value greater than 1 for a particular combination of bacterium with dipeptide therefore indicates that the biofilm growth over 48 hrs was greater than the biofilm growth over 48 hrs for the control.

The experiment was carried out on three different days (thus providing 3 biological replicas) and each day the experiment was carried out in quadruple (thus providing 4 technical replicas) for each combination of bacterium with dipeptide and for each control. For each day and for each combination, the average (mean) of the values obtained (as detailed above) for the four technical replicas was calculated to provide a single value for each combination on each day. The values shown in Tables 7 to 8, below, are the average (mean) of the three single values obtained for each combination of bacterium with dipeptide. The results are shown in Tables 7 to 8, below:

In the above data, a value of 1.6 was taken as the threshold above which the dipeptide caused markedly increased biofilm growth of the bacterium relative to the control. This value was selected in order to exclude low-stimulating metabolites and avoid false positive results.

As can be seen from the above data, Phe-Glu, exhibited prebiotic effects at concentrations of 5 and 10 μmol/ml, and Met-Pro, exhibited prebiotic effects at concentrations of 25, 20 and 10 μmol/ml.

What is claimed is:

1. An oral care composition for contacting the oral cavity comprising:
   (a) a dipeptide selected from: Ser-Asn; Met-Pro; and Phe-Glu, and
   (b) at least on additional oral care ingredient selected from anticaries agents, anticalculus or tartar control agents;
   wherein the composition comprises an amount of dipeptide from 0.01 weight % to 10 weight %, based on the weight of the oral care composition, effective for selectively promoting growth, metabolic activity or colonization of bacteria that have beneficial effects on oral health, relative to growth, metabolic activity or colonization of pathogenic oral bacteria, and selectively promoting biofilm formation by bacteria that have beneficial effects on oral health, relative to biofilm formation by pathogenic oral bacteria.

2. The oral care composition of claim 1, the dipeptide is Ser-Asn.

3. The oral care composition of claim 1, wherein the dipeptide is Met-Pro.

4. The oral care composition of claim 1, wherein the dipeptide is Phe-Glu.

5. A composition according to claim 1, for use in selectively promoting, in an oral cavity: growth, metabolic activity or colonization of bacteria that have beneficial effects on oral health, relative to growth, metabolic activity or colonization of pathogenic oral bacteria.

TABLE 7

Pathogenic bacteria at 48 hours

| | Met-Pro 25 μmol/ml | Met-Pro 20 μmol/ml | Met-Pro 10 μmol/ml | Met-Pro 5 μmol/ml | Phe-Glu 25 μmol/ml | Phe-Glu 20 μmol/ml | Phe-Glu 10 μmol/ml | Phe-Glu 5 μmol/ml |
|---|---|---|---|---|---|---|---|---|
| A actino* | 0.1103 | 0.2556 | 0.5095 | 0.8177 | 0.0212 | 0.0481 | 0.3454 | 0.5867 |
| F nucleatum | 0.5216 | 0.6796 | 0.5568 | 0.6087 | 0.0112 | 0.0056 | 0.2232 | 0.2553 |
| P gingivalis | 0.4990 | 0.8922 | 0.7344 | 0.6831 | 0.3008 | 0.1717 | 0.9004 | 0.7552 |
| P intermedia | 0.1148 | 0.2095 | 0.9773 | 1.2520 | 0.2516 | 0.2103 | 0.1852 | 0.7904 |
| S mutans | 1.3235 | 0.9625 | 0.0118 | 0.0252 | 0.4072 | 1.2009 | 0.5693 | 0.0781 |
| T forsythia | 0.1909 | 0.2726 | 0.4691 | 0.4857 | 0.0254 | 0.0188 | 0.3083 | 0.5744 |

*A actinomycetemcomitans

TABLE 8

Beneficial bacteria over 48 hours

| | Met-Pro 25 μmol/ml | Met-Pro 20 μmol/ml | Met-Pro 10 μmol/ml | Met-Pro 5 μmol/ml | Phe-Glu 25 μmol/ml | Phe-Glu 20 μmol/ml | Phe-Glu 10 μmol/ml | Phe-Glu 5 μmol/ml |
|---|---|---|---|---|---|---|---|---|
| A naeslundii | 0.1281 | 0.4130 | 0.9986 | 1.1703 | 0.0067 | 0.0174 | 0.4234 | 0.9914 |
| C sputigena | 0.0138 | 0.1660 | 0.1949 | 0.2411 | 0.2648 | 0.1578 | 0.1079 | 0.1909 |
| S gordonii | 1.4372 | 1.6395 | 1.8572 | 1.4212 | 0.2237 | 0.6462 | 1.7019 | 1.8315 |
| A viscosus | 0.0355 | 0.1766 | 0.4021 | 0.4286 | 0.0490 | 0.0684 | 1.2242 | 1.3972 |
| S salivarius | 1.4734 | 1.0385 | 0.9847 | 0.8003 | 0.7342 | 0.8978 | 1.0359 | 1.4007 |
| S sanguinis | 1.6580 | 2.1767 | 1.7015 | 1.1768 | 0.4820 | 0.5417 | 1.0551 | 1.2254 |
| V parvula | 0.2121 | 0.1745 | 0.2886 | 0.2845 | 0.2969 | 0.1638 | 0.3136 | 0.3257 |
| S mitis | 0.0464 | 0.2959 | 1.4008 | 1.3974 | 0.1018 | 0.0264 | 0.0179 | 0.7237 |

6. A composition according to claim 1, for use in selectively promoting, in an oral cavity, biofilm formation by bacteria that have beneficial effects on oral health, relative to biofilm formation by pathogenic oral bacteria.

7. A composition according to claim 1, for use in maintaining and/or re-establishing a healthy oral microbiota.

8. A composition according to claim 1, for use in preventing one or more of gingivitis, periodontitis, peri-implantitis, peri-implant mucositis, necrotizing gingivitis, necrotizing periodontitis and caries.

9. A method of selectively promoting, in an oral cavity of a subject: growth, metabolic activity or colonization of bacteria that have beneficial effects on oral health, relative to growth, metabolic activity or colonization of pathogenic oral bacteria; the method comprising contacting the oral cavity with an oral care composition of claim 1.

10. A method of selectively promoting, in an oral cavity of a subject, biofilm formation by bacteria that have beneficial effects on oral health, relative to biofilm formation by pathogenic oral bacteria; the method comprising contacting the oral cavity with an oral care composition of claim 1.

11. A method of maintaining and/or re-establishing a healthy oral microbiota in a subject, the method comprising contacting an oral cavity of the subject with an oral care composition of claim 1.

12. A method of preventing one or more of gingivitis, periodontitis, peri-implantitis, peri-implant mucositis, necrotizing gingivitis, necrotizing periodontitis and caries in a subject, the method comprising contacting an oral cavity of the subject with an oral care composition of claim 1.

* * * * *